United States Patent [19]

Scancarella et al.

[11] Patent Number: 5,643,587
[45] Date of Patent: Jul. 1, 1997

[54] COMPOSITION AND METHOD FOR UNDER-EYE SKIN LIGHTENING

[75] Inventors: Neil D. Scancarella, Wyckoff; John A. Duffy, West Milford, both of N.J.; Mark S. Garrison, White Plains, N.Y.; Gopinathan K. Menon, Wayne, N.J.

[73] Assignee: Avon Products, Inc., Suffern, N.Y.

[21] Appl. No.: 602,004

[22] Filed: Feb. 15, 1996

[51] Int. Cl.[6] .................................................. A61K 7/00
[52] U.S. Cl. .................. 424/401; 424/195.1; 424/62
[58] Field of Search ........................ 424/401, 520, 424/195.1, 62; 514/844, 870, 871, 873, 828, 944, 947

[56] References Cited

U.S. PATENT DOCUMENTS

| | | | |
|---|---|---|---|
| 5,019,391 | 5/1991 | Bunte et al. | 424/195.1 |
| 5,023,090 | 6/1991 | Levin | 424/520 |
| 5,204,105 | 4/1993 | Mausner | 424/401 |
| 5,223,491 | 6/1993 | Donzis | 514/54 |

FOREIGN PATENT DOCUMENTS 7-10734  1/1995  Japan.

OTHER PUBLICATIONS

Roberts, et al., *The Diverse Potential of Yeast*, Biotechnology, 13: 1246 (1995).

*Primary Examiner*—Thurman K. Page
*Assistant Examiner*—Sharon Howard
*Attorney, Agent, or Firm*—Hopgood, Calimafde, Kalil & Judlowe, L.L.P.

[57] ABSTRACT

Disclosed is a composition for topical treatment of skin comprising the use of live yeast cell derivative in combination with a suitable vehicle, for treating discolorations and bagginess in facial skin below the eyes.

18 Claims, No Drawings

COMPOSITION AND METHOD FOR UNDER-EYE SKIN LIGHTENING

FIELD OF INVENTION

The present invention relates to compositions for topical treatment of skin problems associated with abnormal pigmentation. More particularly, the invention comprises the use of live yeast cell derivative in combination with a suitable vehicle, for treating discolorations and bagginess in facial skin below the eyes.

BACKGROUND OF THE RELATED ART

Puffiness or bagginess under the eyes with associated discolorations has many etiologic factors including an abnormal increase in leakage from capillaries beneath the surface of the skin. Fluid accumulating beneath the skin in the region under the eyes results in edema which manifests as baggy eyes often relatively darker in color in contrast to surrounding facial areas which are perceived by consumers as cosmetically unacceptable.

The exact reasons for such increased capillary permeability is not always known, but several factors such as stress, kidney malfunctions, high blood pressure, water retention, excessive consumption of caffeine and lack of sleep have been identified as being associated with the problem. Intrinsic aging and photodamage can also lead to similar changes.

Increased accumulation of "GAG's" (hyaluronic acid & chondroitin sulfate B) can also lead to secondary osmotic changes resulting in increased extra cellular accumulation of protein, sodium and water. In such situations, affected skin appears edematous with pronounced presentation of lymphatics and vessels and microscopically, collagen fibers appear frayed and swollen.

A classic example of acute periorbital edema and discoloration is the "black eye" which results from physical trauma directed to the eye and injury to the skin surrounding the eye. Here, trauma causes leakage of vasculature which manifests as the classical periorbital bruise.

The use of yeast (genus: Saccharomyces) for brewing and baking (species: Saccharomyces cerevisiae) has been recorded throughout history, but its scientific manipulation and the use of derivatives of such technology in cosmetic products is only a recent phenomenon. For instance, U.S. Pat. No. 5,204,105 describes an emulsified cosmetic composition for treatment of skin found below the eyes. The primary components defined in the '105 patent are a mixture of plant and yeast extracts, beta-carotene, vitamin C and a methyl-silanol complex.

The '105 patent disclosure assumes that a mixture of naturally occurring substances will have some (unidentified) benefits to skin, but the '105 patent actually identifies the methyl-silanol complex (not from yeast or plant) as the active ingredient "for minimizing blackness" under the eye.

U.S. Pat. No. 5,223,491 describes the use of an insoluble glucan from yeast cell walls for "revitalizing" skin and Japanese Patent Publication No. 7-10734 (1995) describes the use of a yeast culture isolated from grain and grown in milk for reducing melanocyte-mediated hyperpigmentation. These descriptions are typical of the state-of-the-art which superficially addresses the use of non-animal derived products for skin benefits under the current trend of consumer pressures to use less animal-derived ingredients in cosmetics. A closer reading usually identifies a non-yeast active ingredient or that the wholesome origins such as grain or milk have little to do with its active properties.

There is a need in the art for a functional, therapeutic dermal composition derived from yeast which alleviates discolorations and bagginess found in facial skin below the eyes. To this end, the present invention includes the following goals.

OBJECTS OF THE INVENTION

The object of the present invention is to provide a composition for topical treatment of skin anomalies including puffiness and discolorations found below the eyes.

Another object of the present invention is to provide a composition comprising live yeast cell derivative for reducing under-eye bagginess and associated discolorations.

A further object is to provide a composition containing a selected range of live yeast cell derivative, which also contains selected ranges of magnesium ascorbyl phosphate and vitamin A and E derivatives, to provide therapeutic benefits including reduction of puffiness and discolorations found in skin below the eyes, These and other objects will become evident from the disclosure herein provided.

SUMMARY OF INVENTION

The present invention is a topical formulation for treating under-eye bagginess and associated discolorations which comprises about 0.5 to about 10.0% live yeast cell derivative, about 0.5 to about 10.0% magnesium ascorbyl phosphate, about 0.1 to about 5.0% tocopherol acetate, about 0.01 to about 1.0% retinol palmitate, and a vehicle which maintains the active ingredient levels.

The formulation can be prepared in several different vehicles. For example, a cream embodiment can have about 8.5% emollient oils, about 7.5% various waxes, about 5.0% glycerin, about 3.52% live yeast cell derivative, about 3.0% magnesium ascorbyl phosphate, about 1.0 tocopherol acetate, about 0.5% retinol palmitate, about 0.7% other vitamins and vitamin derivatives, about 2.5% emulsifiers, and about 0.35% thickeners.

A lotion embodiment can have about 10.0% emollient oils, about 5.0% glycerin, about 4.75% various waxes, about 3.5% magnesium ascorbyl phosphate, about 3.25% live yeast cell derivative, about 1.0 tocopherol acetate, about 0.25% retinol palmitate, about 0.8% other vitamins and vitamin derivatives, about 1.75% emulsifiers, and about 0.35% thickeners.

A gel embodiment can have about 1.5% emollient oils, about 1.5% glycerin, about 5.0% live yeast cell derivative, about 2.0% magnesium ascorbyl phosphate, about 0.1 tocopherol acetate, about 0.1% retinol palmitate, about 0.2% other vitamins and vitamin derivatives, about 1.5% emulsifier, and about 0.75% thickeners.

In the above exemplary embodiments, all percentages are expressed by relative weight of ingredient to total weight of composition; glycerin acts as a humectant; emollient oils can include dioctyl maleate, grape and sunflower seed oils, and squalane; various waxes contemplated include soya sterols, glyceryl monostearate, cetyl alcohol and myristyl myristate; other vitamins and vitamin derivatives can include vitamin K and. ascorbyl palmitate; emulsifiers which can be used include PEG 40 stearate, PEG 24 cholsteryl ether and polysorbate 20; and various thickeners such as xantham gum and Carbopols 934 and 941, can also be used.

In addition, topical anti-inflammatories such as bisabilol; neutralizers and pH adjustors such as potassium hydroxide, citric acid and sodium citrate; stabilizers such as silicon dioxide and zeolite; preservatives such as methylparaben, imidazolidinyl urea and benzyl alcohol; anti-oxidants such as BHT; chelators such as tetrasodium EDTA; and various vegetable and botanical extracts and fragrances known to those skilled in the art, can all be employed in diverse combinations to enhance the efficacy of and impart general skin benefits to the present invention.

The topical compositions which comprise the present invention contain live yeast cell derivative (hereinafter also "LYCD") as the active ingredient in an appropriate formulation for treating under-eye problems such as dark circles and bagginess. As noted above, dark under-eye circles are not a simple melanocyte mediated pigmentation problem. Etiologies include circulatory malfunctions, inflammation and exposure to the environment, and the problem does not respond well to known hypopigmenting or skin whitening compounds. The LYCD-containing compositions of the present invention provide a practical alternative for treating dark undereye circles.

LYCD is a highly complex, low molecular weight, biologically active material comprised of amino acids, monosaccharides and disaccharides, and trace quantities of vitamins and minerals. LYCD as used in the present invention is produced from live yeast cultures of Saccharomyces cerevisiae and consists primarily of glycosidic and peptidic fractions resulting from proteolytic extraction of living yeast cells subjected to ultra-violet (UV) stress which causes the cells to synthesize "protective" chemical entities. These active substances promote oxygen uptake and enhance the metabolic processes within human cells. For example, these materials have been reported to enhance collagen production in fibroblasts. Brooks et al., *Live Yeast Cell Derivative*, Cosmetics & Toiletries, 110:65–70 (1995).

As noted above, the present formulations can also contain vitamins A, C, E and K and their derivatives, phospholipids and bisabolol to promote other cosmetic benefits. Additionally, LYCD when combined with magnesium ascorbyl phosphate (MAP), tocopherol acetate and retinol palmitate, produces surprising benefits for lightening dark undereye circles. Regular topical use, twice daily of such active blends produce dramatic, tangible improvements in dark undereye circles within two weeks.

DETAILED DESCRIPTION OF THE INVENTION

The theory behind live yeast cell derivative (LYCD) is based on a living cell's response to trauma. An injured cell reflexively produces self-protective substances. LYCD used in this disclosure is manufactured from living yeast cell cultures by modifying their medium to select for metabolic processes which produce a particularly useful, safe, cosmetic quality material.

Yeast cultures are placed in a fermenter and brought to viability in an appropriate nutrient media with thorough aeration under a controlled temperature. The living yeast cells are then. stressed with UV light (286 nm). The cells respond by producing various protective substances. The cells' biochemical changes can be monitored by assaying absorption at 256 to 258 nm with a UV spectrophotometer. Exposure to UV light is continued, for up to several days, until the complex biochemical protective mechanism is complete. Fermentation is brought to a halt by breaking down cell walls with a suitable proteolytic enzyme. Insoluble cell wall material is separated with centrifuge and cellular protoplasm is harvested. The soluble protoplasmic extract is then concentrated and assayed for biological activity.

The LYCD extract can either be concentrated by freeze drying or spray drying, and is usually available as a filtered, cosmetic grade solution such as from Brooks Inc., South Plainfield, N.J. Extensive analysis has shown that the LYCD consists of low molecular weight peptide/glycosidic fractions between 400 to 3,500 daltons with the peptide to glycosidic ratio being approximately 3:1. The glycopeptide linkages are through the orthoglycosidic, asparagine residues. There are also trace quantities of coenzyme-type vitamins typical of yeast present, along with cofactor-type minerals. Brooks et al., Id.

The following exemplary embodiments were made pursuant to the present invention.

TABLE 1

|  | CREAM | LOTION | GEL |
| --- | --- | --- | --- |
| Live Yeast Cell Extract | 3.52 | 3.25 | 5.00 |
| Magnesium Ascorbyl Phosphate | 3.00 | 3.50 | 2.00 |
| Vitamin K | 0.50 | 0.50 | 0.10 |
| Ascorbyl Palmitate | 0.20 | 0.30 | 0.10 |
| Tocopherol Acetate | 1.00 | 1.00 | 0.10 |
| Bisabilol | 0.50 | 0.25 | 0.10 |
| Vitamin A Palmitate | 0.50 | 0.25 | 0.10 |
| Soy Lecithin/Cholesterol Blend | 0.20 | 0.15 | 0.05 |
| Demineralized Water | 55.82 | q.s. | q.s. |
| Carbopol 934 | 0.25 |  | 0.75 |
| Carb 941 |  | 0.25 |  |
| Xantham Gum | 0.10 | 0.10 |  |
| Glycerin | 5.00 | 5.00 | 1.50 |
| Potassium Hydroxide | 0.25 | 0.25 | 0.65 |
| Glyceryl Monostearate | 2.50 | 1.50 |  |
| Cetyl Alcohol | 2.00 | 1.00 |  |
| Myristyl Myristate | 2.00 | 2.00 |  |
| PEG 40 Stearate | 2.00 | 1.50 |  |
| Soya Sterols | 1.00 | 0.25 |  |
| PEG 24 Cholsteryl Ether | 0.50 | 0.25 |  |
| Silicon Dioxide | 0.43 | 0.25 |  |
| Methylparaben | 0.40 | 0.40 | 0.25 |
| BHT | 0.15 | 0.15 | 0.05 |
| Dioctyl Maleate | 2.55 | 2.50 | 0.50 |
| Grape Seed Oil | 2.13 | 3.00 | 0.50 |
| Sunflower Seed Oil | 2.13 | 2.50 | 0.50 |
| Squalane | 1.70 | 2.00 |  |
| Corn Starch Ester | 1.87 | 1.00 | 0.25 |
| Silica Bead | 1.70 | 1.00 |  |
| Zeolite | 0.85 | 0.50 | 0.25 |
| Sodium Citrate | 1.00 | 1.00 |  |
| Citric Acid | 0.20 | 0.20 |  |
| Tetra Sodium EDTA | 0.20 | 0.15 | 0.10 |
| Imidazolidinyl Urea | 0.50 | 0.40 | 0.50 |
| Cyclomethicone Tetramer | 2.55 | 2.00 |  |
| Benzyl Alcohol | 0.50 | 0.50 | 0.25 |
| Fragrances | 0.30 | 0.25 | 0.10 |
| Polysorbate 20 |  |  | 1.50 |

The exemplary embodiments shown in Table 1 serve only to illustrate but not limit the invention. One skilled in the art could easily apply the disclosure provided herein to develop further embodiments and other suitable vehicles without departing from the scope of this invention. The above-listed exemplary embodiments were made following a protocol similar to that out-lined below which is for the cream embodiment.

EXAMPLE 1

Preparation of Cream Formula

The primary equipment used to make the cream embodiment was a Pressindustria/Eppenbach with an equipment capacity of 60–90% by volume. Auxiliary equipment included three side kettles, kettle no. 1 with 30% by volume, kettle no. 2 with 30% by volume, and kettle no. 3 with 35% by volume. Batches made in the Pressindustria/Eppenbach equipment used high speed milling when milling is specified below.

Demineralized water (20.82 wt.%) was added to side kettle no. 1. With moderate mixing, glycerin and tetrasodium EDTA was next added and mixed for 5 to 10 minutes until uniform consistency was achieved. Carbopol 934 was then slowly sprinkled into kettle no. 1 and vigorously mixed for 60–90 minutes, until uniform.

Xantham gum was slowly sprinkled into side kettle no. 1 and vigorously mixed for 60–90 minutes, until uniform. The contents of side kettle no. 1 were then strained (200 microns or finer) into the Pressindustria/Eppenbach and heated to 170°–175° F. (77°–79° C.) with mixing.

Demineralized water (0.67 wt.%) was poured into side kettle no. 1 and heated to 170°–175° F. (77°–79° C.), then transfered through a strainer (200 microns or finer) into the Pressindustria/Eppenbach, thereby flushing side kettle no. 1 and connecting pumps and lines.

A premix of 1.0 wt.% demineralized water and the potassium hydroxide was made in a suitable container and transferred into the Pressindustria/Eppenbach. Temperature was maintained at 170°–175° F. (77°–79° C.) with good mixing.

Vitamin A palmitate, glyceryl monostearate, cetyl alcohol, myristyl myristate, PEG 40 stearate, soya sterols, PEG 24 cholsteryl ether, silicon dioxide, methylparaben, BHT, dioctyl maleate and squalane were slowly added into side kettle no. 2 and heated to 190°–195° F. (88°–91° C.) and mixed until uniform.

Ascorbyl palmitate, tocopherol acetate, bisabilol, soy lecithin/cholesterol blend, grape and sunflower seed oils were next slowly added to side kettle no. 2 with temperature maintained between 170°–175° F. (77°–79° C.) and mixed for 15–20 minutes.

Corn starch ester, silica bead and zeolite was then added to side kettle no. 2 with temperature maintained between 170°–175° F. (77°–79° C.) and mixed, then the contents of kettle no. 2 was transferred to the Pressindustria/Eppenbach. Heat was maintained at 170°–175° F (77°–79° C.) with good mixing. Demineralized water (0.66 wt.%) was poured into side kettle no. 2 and heated to 170°–175° F. (77°–79° C.), then transfered into the Pressindustria/Eppenbach to flush side kettle no. 2, connecting pumps and lines.

The batch in the Pressindustria/Eppenbach was milled for 5 minutes and mixed for 10–15 minutes while maintaining the temperature at 170°–175° F. (77°–79° C.). The batch was next cooled to 120°–125° F. (49°–52° C.) while mixing.

Thirty (30) wt.% demineralized water was added to side kettle no. 3 and heated to 120°–125° F. (49°–52° C.). Sodium citrate and citric acid were added to the water and mixed until uniform. The magnesium ascorbyl phosphate was added by sprinkling very carefully to side kettle no. 3 and mixed with temperature not exeeding 125° F. (52° C.). Vitamin K was next added and mixed for 5–10 minutes until uniform. With the mill turned on, the contents of side kettle no. 3 were strained (200 microns or finer) into the Pressindustria/Eppenbach. Demineralized water (0.67 wt.%) was poured into side kettle no. 3, then transfered through a strainer (200 microns or finer) into the Pressindustria/ Eppenbach to flush side kettle no. 3, connecting pumps and lines.

The batch was milled for 5 minutes and slowly mixed for 10–15 minutes until uniform, then cooled to 115°–120° F. (46°–49° C.) while continuing to mix slowly. A premix of 2.0 wt.% demineralized water, imidazolidinyl urea and LYCD was made in a suitable container until uniform and transferred into the Pressindustria/Eppenbach. The batch was slowly mixed for 10–15 minutes until uniform. Cyclomethicone tetramer and benzyl alcohol were next added into the Pressindustria/Eppenbach and slowly mixed for 10–15 minutes until uniform.

EXAMPLE 2

Undereye Treatment Study

Under the supervision of a dermatologist, the cream formulation as specified above was tested on a panel of 50 women who had discolorations and bagginess in facial skin below the eyes. More specifically, some panelists had "dermal circles" which researchers classified as discolorations and bagginess resulting from blood leaking from capillaries into the surrounding tissue. Other contributing factors for dermal circles were attributed to visibility of capillary walls or dilation of blood vessels in panelists with relatively more transparent skin. The bluish-purple effect in the undereye area of those with dermal circles was most pronounced in fairer-skinned panelists.

Another category of discoloration manifested was a "mixed" type wherein panelists exhibited a combination of dermal and "epidermal" circles. In addition to dermal circles, mixed types also had hyperpigmentation which was more common in the darker-skinned panelists and those with fair skin who were prone to freckling. Age and photodamage accentuated the effects.

The cream was applied in a split face fashion, i.e. one undereye area (left or right) received the active cream while the other undereye area was untreated. The topical treatment application was twice per day under blinded, random assignment conditions. Specifically, the cream was applied to the entire under-eye, "crowsfeet" and upper cheek bone areas, twice a day (AM and PM) for the entire study. No other skin care products were used underneath either eye area during the study. The panelists were instructed to cleanse their faces as per normal routine, and each AM and PM to dispense 1 to 2 dots of cream onto fingertips and gently apply underneath the designated eye, crowsfeet and upper cheek bone areas.

The dermatologist examined the undereye areas of the inventive cream application sites and compared it to the corresponding control sites at 2, 4, 8 and 12 week intervals. The intensity of color in the undereye area on which the cream containing LYCD was applied was significantly reduced in the majority of panelists as early as two weeks after application. Inprovements in lines and. texture, a decrease in puffiness of the suborbital area, and reductions in color intensity and in color area were observed in the majority of panelists four weeks after application (see Tables 2–4, below).

A reduction in color intensity meant that the affected skin achieved a lighter tone, and a reduction in color area meant a decrease in the amount or extent of coloration, with improvements begining from outer areas (corner of eye and top of cheek) and receding towards the undereye lid area. Table 2, below, gives a scaled score for different parameters tested.

TABLE 2

| Parameter | Baseline | 2 Weeks | 4 Weeks | 8 Weeks | 12 Weeks |
|---|---|---|---|---|---|
| Color Degree | 0 | 1.0 | 2.3 | 2.3 | 2.4 |
| Color Area | 0 | 0.7 | 1.8 | 2.1 | 2.0 |
| Suborbital Lines | 0 | 0.1 | 1.3 | 2.1 | 2.1 |
| Texture | 0 | 0.2 | 1.5 | 2.0 | 2.2 |
| Puffiness | 0 | 0 | 0.5 | 0.6 | 0.6 |
| Lentigines | 0 | 0.4 | 0.6 | 0.8 | 1.0 |
| Elasticity | 0 | 0 | 0 | 0 | 0 |

Table 3, below, shows the percentage (%) of tested panelists showing improvement at each time point.

TABLE 3

| Parameter | Baseline | 2 Weeks | 4 Weeks | 8 Weeks | 12 Weeks |
|---|---|---|---|---|---|
| Color Degree | 0 | 49 | 83 | 95 | 100 |
| Color Area | 0 | 40 | 76 | 91 | 100 |
| Suborbital Lines | 0 | 6 | 60 | 98 | 100 |
| Texture | 0 | 12 | 73 | 98 | 100 |
| Puffiness | 0 | 0 | 27 | 37 | 48 |
| Lentigines | 0 | 34 | 46 | 62 | 76 |
| Elasticity | 0 | 0 | 0 | 0 | 0 |

Table 4, below, summarizes combined sensory and clinical data.

TABLE 4

| | CHANGE | AFTER 2 WEEKS | AFTER 4 WEEKS | AFTER 8 WEEKS | AFTER 12 WEEKS |
|---|---|---|---|---|---|
| TEXTURE | makes skin feel smoother | ✓ | ✓<br>↑ in 73% | ✓<br>98% | 100%<br>100% |
| TONE | helps firm delicate eye area | ✓ | ✓ | ✓ | |
| | makes skin feel more supple, more elastic, more resilient | ✓ | ✓ | ✓ | |
| MOISTURE | provides long-lasting moisture | ✓ | ✓ | ✓ | |
| FINE LINES AND WRINKLES | diminishes appearance of fine lines and wrinkles | | ✓<br>↑ in 60% | ✓<br>98% | 100% |
| | softens and smooths fine lines and wrinkles | ✓ | ✓ | ✓ | |
| DARK CIRCLES | make dark circles appear less noticeable | | (area)<br>↑ in 76% | ✓ | |
| | significantly lightens dark circles | | (degree)<br>↑ in 83% | | |
| PUFFINESS, BAGS | diminishes the appearance of puffiness | | ✓ | ✓ | ↑ in 48% |
| | diminishes the appearance of unsightly bags | | | | |
| YOUTH | helps skin around the eye look younger | | ✓ | ✓ | |
| HEALTH | is nourishing to skin | ✓ | ✓ | ✓ | |
| | helps the skin around the eye look healthier | ✓ | ✓ | ✓ | |

↑ = IMPROVEMENT, PER DERMATOLOGIST'S EVALUATION;
✓ = SIGNIFICANT FINDING; PANELIST OPINION
TESTS SHOW:
After 2 weeks: Skin around eyes looks smoother; fine lines and wrinkles are softened.+
After 4 weeks: Dark circles appear lighter in 8 out of 10 panelists* and puffiness is diminished.+
After 8 weeks: Dark circles are significantly less noticeable.+
+sensory finding; *clinical finding Various modifications and alterations to the present invention may be appreciated based on a review of this disclosure. These changes and additions are intended to be within the scope and spirit of this invention as defined by the following claims.

What is claimed is:

1. A composition for topical treatment of skin discolorations found below the eyes, comprising:
    (a) about 0.5 to about 10.0% live yeast cell extract,
    (b) about 0.5 to about 10.0% magnesium ascorbyl phosphate,
    (c) about 0.1 to about 5.0% tocopherol acetate,
    (d) about 0.01 to about 1.0% retinol palmitate, and
    (e) a vehicle which maintains active ingredient levels.

2. The composition of claim 1, comprising:
    (a) about 8.5% emollient oils,
    (b) about 7.5% waxes,
    (c) about 5.0% glycerin,
    (d) about 3.52% live yeast cell extract,
    (e) about 3.0% magnesium ascorbyl phosphate,
    (f) about 1.0 tocopherol acetate,
    (g) about 0.5% retinol palmitate,
    (h) about 0.7% vitamins,
    (i) about 2.5% emulsifiers, and
    (j) about 0.35% thickeners.

3. The composition of claim 2, wherein said emollient oils are selected from the group consisting of dioctyl maleate, grape and sunflower seed oils, and squalane; said waxes are selected from the group consisting of soya sterols, glyceryl monostearate, cetyl alcohol and myristyl myristate; said vitamins is vitamin K; said emulsifiers are selected from the group consisting of PEG 40 stearate, PEG 24 cholsteryl ether and polysorbate 20; and said thickeners are selected from the group consisting of xantham gum, Carbopols 934 and 941 and further comprising ascorbyl palmitate.

4. The composition of claim 1, comprising:
    (a) about 10.0% emollient oils,
    (b) about 5.0% glycerin,
    (c) about 4.75% waxes,
    (d) about 3.5% magnesium ascorbyl phosphate,
    (e) about 3.25% live yeast cell extract,
    (f) about 1.0 tocopherol acetate,
    (g) about 0.25% retinol palmitate,
    (h) about 0.8% vitamins,
    (i) about 1.75% emulsifiers, and
    (j) about 0.35% thickeners.

5. The composition of claim 4, wherein said emollient oils are selected from the group consisting of dioctyl maleate, grape and sunflower seed oils, and squalane; said waxes are selected from the group consisting of soya sterols, glyceryl monostearate, cetyl alcohol and myristyl myristate; said vitamins is vitamin K; said emulsifiers are selected from the group consisting of PEG 40 stearate, PEG 24 cholsteryl ether and polysorbate 20; and said thickeners are selected from the group consisting of xantham gum, Carbopols 934 and 941 and further comprising ascorbyl palmitate.

6. The composition of claim 1, comprising:
    (a) about 1.5% emollient oils,
    (b) about 1.5% glycerin,
    (c) about 5.0% live yeast cell extract,
    (d) about 2.0% magnesium ascorbyl phosphate,
    (e) about 0.1 tocopherol acetate,
    (f) about 0.1% retinol palmitate,
    (g) about 0.2% vitamins,
    (h) about 1.5% emulsifier, and
    (j) about 0.75% thickeners.

7. The composition of claim 6, wherein said emollient oils are selected from the group consisting of dioctyl maleate, grape and sunflower seed oils, and squalane; said vitamins is vitamin K; said emulsifiers are selected from the group consisting of PEG 40 stearate, PEG 24 cholsteryl ether and polysorbate 20; and said thickeners are selected from the group consisting of xantham gum, Carbopols 934 and 941 and further comprising ascorbyl palmitate.

8. A method for topical treatment of skin discolorations found below the eyes comprising the application of a composition comprised of:
    (a) about 0.5 to about 10.0% live yeast cell extract,
    (b) about 0.5 to about 10.0% magnesium ascorbyl phosphate,
    (c) about 0.09 to about 0.6% retinol palmitate,
    (d) about 0.1 to about 5.0% tocopherol acetate, and
    (e) a vehicle which maintains active ingredient levels.

9. The method of claim 8, wherein said composition comprises:
    (a) about 8.5% emollient oils,
    (b) about 7.5% waxes,
    (c) about 5.0% glycerin,
    (d) about 3.52% live yeast cell extract,
    (e) about 3.0% magnesium ascorbyl phosphate,
    (f) about 1.0 tocopherol acetate,
    (g) about 0.5% retinol palmitate,
    (h) about 0.7% vitamins,
    (i) about 2.5% emulsifiers, and
    (j) about 0.35% thickeners.

10. The method of claim 9, wherein said emollient oils are selected from the group consisting of dioctyl maleate, grape and sunflower seed oils, and squalane; said waxes are selected from the group consisting of soya sterols, glyceryl monostearate, cetyl alcohol and myristyl myristate; said vitamins is vitamin K; said emulsifiers are selected from the group consisting of PEG 40 stearate, PEG 24 cholsteryl ether and polysorbate 20; and said thickeners are selected from the group consisting of xantham gum, Carbopols 934 and 941 and further comprising ascorbyl palmitate.

11. The method of claim 8, wherein said composition comprises:
    (a) about 10.0% emollient oils,
    (b) about 5.0% glycerin,
    (c) about 4.75% waxes,
    (d) about 3.5% magnesium ascorbyl phosphate,
    (e) about 3.25% live yeast cell extract,
    (f) about 1.0 tocopherol acetate,
    (g) about 0.25% retinol palmitate,
    (h) about 0.8% vitamins,
    (i) about 1.75% emulsifiers, and
    (j) about 0.35% thickeners.

12. The method of claim 11, wherein said emollient oils are selected from the group consisting of dioctyl maleate, grape and sunflower seed oils, and squalane; said waxes are selected from the group consisting of soya sterols, glyceryl monostearate, cetyl alcohol and myristyl myristate; said vitamins is vitamin K; said emulsifiers are selected from the group consisting of PEG 40 stearate, PEG 24 cholsteryl ether and polysorbate 20; and said thickeners are selected from the group consisting of xantham gum, Carbopols 934 and 941 and further comprising ascorbyl palmitate.

13. The method of claim 8, wherein said composition comprises:
(a) about 1.5% emollient oils,
(b) about 1.5% glycerin,
(c) about 5.0% live yeast cell extract,
(d) about 2.0% magnesium ascorbyl phosphate,
(e) about 0.1 tocopherol acetate,
(f) about 0.1% retinol palmitate,
(g) about 0.2% vitamins and vitamin derivatives,
(h) about 1.5% emulsifier, and
(j) about 0.75% thickeners.

14. The method of claim 13, wherein said emollient oils are selected from the group consisting of dioctyl maleate, grape and sunflower seed oils, and squalane; said vitamins is vitamin K; said emulsifiers are selected from the group consisting of PEG 40 stearate, PEG 24 cholsteryl ether and polysorbate 20; and said thickeners are selected from the group consisting of xantham gum, Carbopols 934 and 941 and further comprising ascorbyl palmitate.

15. A composition for topical treatment of skin discolorations found below the eyes, comprising:
(a) about 0.5 to about 10.0% live yeast cell extract,
(b) about 0.5 to about 10.0% magnesium ascorbyl phosphate, and
(c) a vehicle which maintains active ingredient levels.

16. The composition of claim 15, further comprising about 0.1 to about 5.0% tocopherol acetate.

17. The composition of claim 15, further comprising about 0.01 to about 1.0% retinol palmitate.

18. A method for topical treatment of skin discolorations found below the eyes comprising the application of a composition comprised of live yeast cell extract and a vehicle which maintains active ingredient levels.

* * * * *